United States Patent

Baumann et al.

[11] 4,147,509
[45] Apr. 3, 1979

[54] PRESSURE-SENSITIVE RECORDING MATERIAL

[75] Inventors: Hans Baumann, Wachenheim; Andreas Oberlinner, Ludwigshafen, both of Fed. Rep. of Germany

[73] Assignee: BASF Aktiengesellschaft, Rheinland-Pfalz, Fed. Rep. of Germany

[21] Appl. No.: 868,211

[22] Filed: Jan. 9, 1978

[30] Foreign Application Priority Data

Jan. 29, 1977 [DE] Fed. Rep. of Germany ....... 2703811

[51] Int. Cl.² .................... D06P 5/00; B41L 1/16
[52] U.S. Cl. .............................. 8/18 R; 8/7; 282/27.5; 282/28 R; 427/150; 427/151; 427/153
[58] Field of Search .............. 8/18 R; 427/151; 282/27.5, 28 R

[56] References Cited

U.S. PATENT DOCUMENTS

| | | | |
|---|---|---|---|
| 2,548,366 | 4/1951 | Green et al. | 282/27.5 |
| 2,800,457 | 7/1957 | Green et al. | 252/316 |
| 3,103,404 | 9/1963 | Salvin et al. | 8/174 |
| 4,069,353 | 1/1978 | Matsukawa et al. | 427/151 |

FOREIGN PATENT DOCUMENTS 50-1746 1/1975 Japan.

*Primary Examiner*—A. Lionel Clingman
*Attorney, Agent, or Firm*—Oblon, Fisher, Spivak, McClelland & Maier

[57] ABSTRACT

A pressure-sensitive recording material which comprises a substrate bearing a dye-forming component and a binder. The dye-forming component is a spirodipyran of the formula

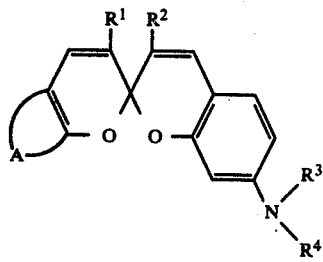

where A is the radical of a fused benzene or naphthalene ring (which rings may or may not be substituted), $R^1$ is alkyl of 1 to 16 carbon atoms, substituted or unsubstituted phenyl or phenalkyl of 7 to 10 carbon atoms, $R^2$ is H or together with $R^1$ is a trimethylene or tetramethylene bridge which is unsubstituted or substituted by from 1 to 3 alkyl, $R^3$ is benzyl or β-phenylethyl and $R^4$ is benzyl, β-phenylethyl or substituted or unsubstituted phenyl, or $R^3$ is alkyl of 1 to 4 carbon atoms and $R^4$ is substituted or unsubstituted phenyl or $R^3$ is benzyl and $R^4$ is β-cyanoethyl. The recording materials give violet to bluish green colorations (copies) only on paper coated with an electron acceptor.

11 Claims, No Drawings

PRESSURE-SENSITIVE RECORDING MATERIAL

The present invention relates to a pressure-sensitive recording material.

Japanese Laid-Open Application 1,746/1975 discloses some compounds of the formula I given below. According to this publication, the compounds are used for the manufacture of thermographic recording materials.

We have found that the compounds of the formula I are exceptionally suitable for use in pressure-sensitive recording materials, since the dye-forming components show little or very little tendency to produce a color on uncoated base paper.

Accordingly, the present invention relates to a pressure-sensitive recording material which comprises a substrate bearing, as a dye-forming component, a compound of the general formula I

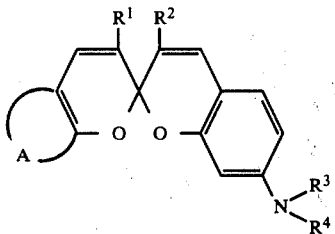

where A is the radical of a fused benzene ring which is unsubstituted or substituted by alkyl of 1 to 4 carbon atoms, alkoxy of 1 to 4 carbon atoms, nitro, chlorine, bromine or carbo-alkoxy (where alkoxy is of 1 to 6 carbon atoms) or is the radical of a naphthalene ring which is fused in the 2,1-position and is unsubstituted or substituted by chlorine, bromine or carbo-alkoxy (where alkoxy is of 1 to 6 carbon atoms), $R^1$ is alkyl of 1 to 16 carbon atoms, phenyl, which is unsubstituted or substituted by alkyl of 1 to 4 carbon atoms, alkoxy of 1 to 4 carbon atoms, chlorine or bromine, or phenylalkyl of 7 to 10 carbon atoms, $R^2$ is hydrogen or $R^1$ and $R^2$ together are a trimethylene or tetramethylene bridge, where one, two or three H atoms may be replaced by alkyl of 1 to 12 carbon atoms, $R^3$ is benzyl or $\beta$-phenylethyl and $R^4$ is benzyl, $\beta$-phenylethyl or phenyl which is unsubstituted or substituted by chlorine, bromine, alkyl of 1 to 4 carbon atoms, methoxy or ethoxy, $R^3$ and $R^4$ being identical or different, or $R^3$ is alkyl of 1 to 4 carbon atoms and $R^4$ is phenyl which is unsubstituted or substituted by chlorine, bromine, alkyl of 1 to 4 carbon atoms, methoxy or ethoxy, or $R^3$ is benzyl and $R^4$ is $\beta$-cyanoethyl.

Specific examples of substituents $R^1$ are methyl, ethyl, propyl, isopropyl, butyl, isobutyl, pentyl, isopentyl, hexyl, isohexyl, n-octyl, isooctyl, 2-ethylhexyl, nonyl, decyl, dodecyl, tetradecyl, hexadecyl, phenyl, 4-methylphenyl, 4-chlorophenyl, 4-bromophenyl, 4-ethylphenyl, 4-isopropylphenyl, 4-methoxyphenyl, 4-ethoxyphenyl, benzyl, $\beta$-phenylethyl, $\gamma$-phenylpropyl, $\beta$-phenylpropyl and $\delta$-phenylbutyl.

Preferably, $R^1$ is alkyl of 1 to 4 carbon atoms.

$R^1$ and $R^2$ can together form a trimethylene or tetramethylene bridge, which is unsubstituted or substituted by alkyl. Specific examples are trimethylene, $\beta,\gamma,\gamma$-trimethyltrimethylene, $\gamma$-tert.-butyltrimethylene, $\gamma$-isopentyltrimethylene, $\gamma$-n-pentyltrimethylene, $\gamma$-n-octyltrimethylene, $\gamma$-n-nonyltrimethylene, $\gamma$-n-dodecyltrimethylene, $\gamma$-hexadecyltrimethylene and tetramethylene.

Preferred dye-forming components of the formula I are those where $R^3$ and $R^4$ are benzyl and/or $\beta$-phenylethyl or $R^3$ is alkyl of 1 to 4 carbon atoms and $R^4$ is phenyl which is substituted in the 4-position by chlorine or alkyl of 1 to 4 carbon atoms.

The spirodipyrans of the formula I are slightly colored or colorless compounds; their solutions in an inert organic solvent give colorations ranging from reddish violet to blue in contact with electron-attracting materials. Typical examples of electron acceptors are carboxylic acids and mineral acids, kaolin, bentonite, activated clay, aluminum silicate, attapulgite or any clay, acidic polymeric materials, eg. condensation products of phenols and/or phenolsulfonic acids, and metal oxides and metal salts, eg. zinc oxide, aluminum oxide, zinc chloride, iron stearate and cobalt naphthenate.

Because of these properties, the compounds of the formula I may be used as dye-forming components for pressure-sensitive recording materials or copying materials.

Preferably, the pressure-sensitive recording materials of the invention contain the dye-forming components in the form of a solution or suspension in organic solvents, eg. chloroparaffins, halogenated or partially hydrogenated biphenyl, alkylbenzenes, alkylnaphthalenes, alkylated dibenzylbenzene, paraffin oil, mineral oil or conventional solvents, eg. toluene or xylene, the solution or suspension being enclosed in microcapsules. In contact with an electron acceptor, a coloration ranging from reddish violet to blue is produced on rupturing the capsules, eg. under writing or typing pressure.

Suitable processes for the manufacture of microcapsules are described, for example, in U.S. Pat. Nos. 2,800,457 and 2,800,458 (gelatin capsules) and in German Published Application No. DAS 2,119,933 (polymer capsules).

Since the dye-forming components to be used for the recording material according to the invention are also more stable in aqueous suspension than are dye-forming components containing dialkylamino groups, the former give virtually colorless microcapsule dispersions.

To produce a pressure-sensitive recording material coated with microcapsules, the aqueous microcapsule dispersion obtained is mixed with binders conventionally used in paper processing, with or without other additives, for instance spacer materials, eg. cellulose powders or cellulose flour, protective colloids or compounds which stabilize the viscosity of the microcapsule dispersion, the mixture is then applied to the substrate, eg. paper, and the coated substrate is dried.

The microcapsule dispersion can be applied to the substrate by brush coating, eg. by means of an air-knife, or by means of printing processes, eg. using printing cylinders carrying numerous deep and closely packed gravure cells.

Suitable substrates are sheet materials, preferably paper. For the purposes of the invention, paper not only means paper produced from cellulose fibers but also paper in which these fibers are partially or completely replaced by synthetic fibers made from polymers.

The recording material according to the invention may also contain the dye-forming component in a finely divided form in wax or in an oil-wax mixture. A recording material of this type can be produced by coating substrates, eg. films or paper, for example using the process described in U.S. Pat. No. 3,103,404. Pressure-sensitive materials are obtained, which can be used for making copies on papers coated with electron acceptors, and which are removed, like carbon paper, after use.

The compounds of the formula I, contained in the recording material according to the invention, have the advantage, when used in pressure-sensitive copying systems, that the dye-forming component shows virtually no tendency to form a color on base paper which has not been coated with an electron acceptor, or on conventional paper. Hence, on making the copy, no mirror image is produced on the face of the substrate which is coated with the dye-forming component. For the same reason, unintentional destruction of the capsules causes no staining of the face of the sheet which carries the microcapsules.

For technological reasons, particularly preferred dye-forming components for the recording materials are spirodipyrans of the formula

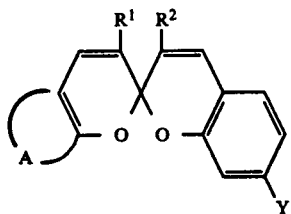

where Y is

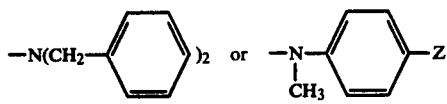

where Z is chlorine or alkyl of 1 to 4 carbon atoms, and A, $R^1$ and $R^2$ have the above meanings. Amongst these compounds, those where $R^2$ is hydrogen and $R^1$ is alkyl of 1 to 4 carbon atoms are particularly preferred.

For tinctorial and technological reasons, recording materials which contain dye-forming components of the formula Ia, where $R^2$ is hydrogen, $R^1$ is alkyl of 1 to 4 carbon atoms, Y is N,N-dibenzylamino or N-methyl-N-p-tolyl-amino and A is the radical of a fused benzene ring or 2,1-naphthalene ring, are particularly preferred. Specific examples of exceptionally preferred dye-forming components are

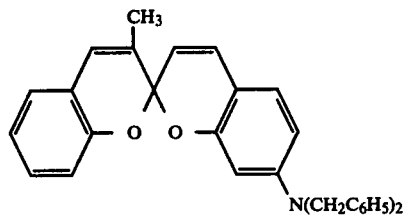

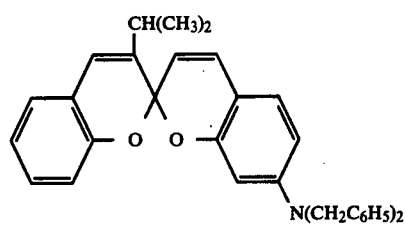

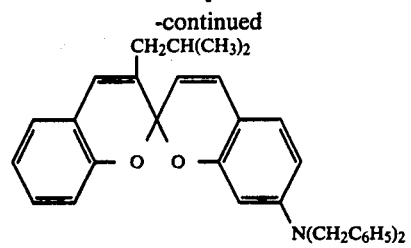

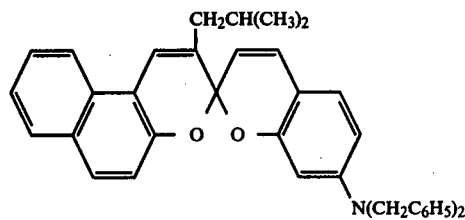

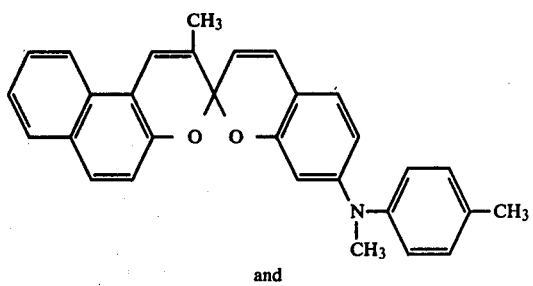

and

-continued

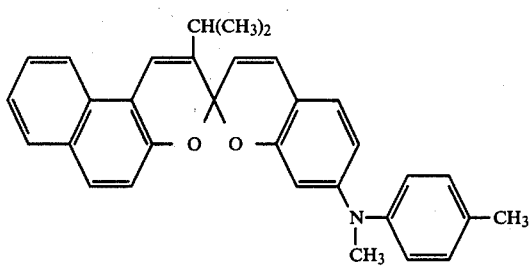

The dye-forming components I are synthesized in the conventional manner by cyclizing the o-hydroxylarylstyryl compounds of the formula IV. The latter are obtained by, for example, condensing benzopyrylium salts of the formula II with N-substituted p-aminosalicylaldehydes of the formula III. The compounds of the formula IV can also be manufactured by the conventional method of reacting the chalkones of the formula V with aldehydes of the formula III in accordance with the scheme shown below:

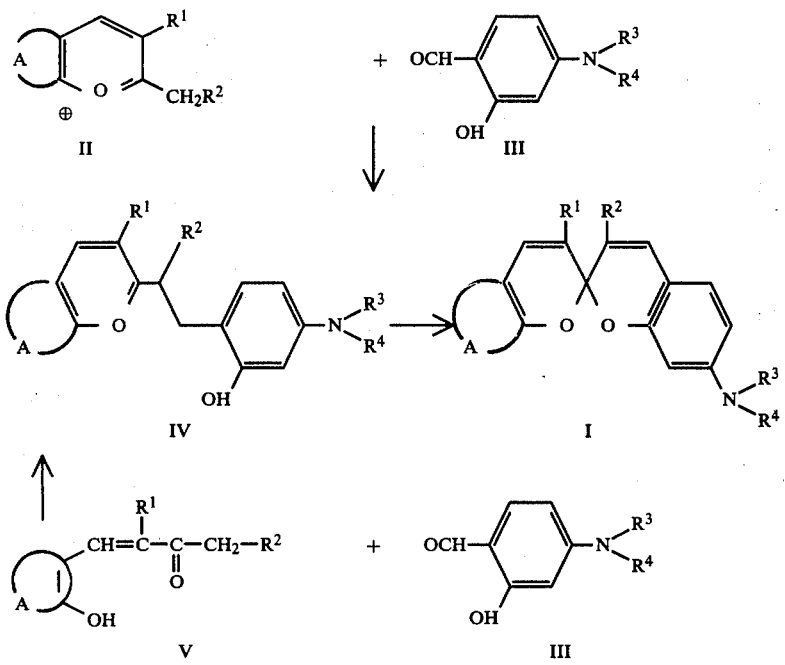

The condensation is advantageously carried out in inert organic solvents which are liquid at the reaction temperature, eg. alcohols, carboxylic acids, carboxylic acid anhydrides, carboxylic acid amides, hydrocarbons or acetonitrile, in the presence or absence of acid or basic condensing agents, eg. zinc chloride, phosphoric acid, hydrogen chloride, toluenesulfonic acid, boric acid, pyridine, piperidine, triethylamine or ammonium acetate, in amounts conventionally used for condensation reactions of the present type.

As a rule, the condensation is carried out at from 20° to 120° C.

The cyclization to give the pyran derivative can be carried out simultaneously with the condensation or subsequently thereto, in the same or a separate step, in the presence or absence of a base, eg. sodium hydroxide or potassium hydroxide, sodium carbonate or potassium carbonate, sodium acetate or potassium acetate, ammonia, aliphatic amines or pyridine. The crystalline spirodipyran compound which separates out from this solution can be used as a dye-forming component either directly or after purification, eg. by recrystallization or reprecipitation.

Examples of suitable starting compounds of the formulae II, III and V for the manufacture of the compounds (IV) are:

(a) Pyrylium salts of the formula II in the form of their chlorides, perchlorates, tetrafluoborates, tetrachloroferrates and trichlorozincates: 2,3-dimethyl-benzopyrylium salt, 2-methyl-3-i-propyl-benzopyrylium salt, 2-methyl-3-i-butyl-benzopyrylium salt, 2,3-tetramethylene-benzopyrylium salt, 2-methyl-3-decyl-benzopyrylium salt, 2-methyl-3-i-pentyl-benzopyrylium salt, 2-methyl-3-n-pentyl-benzopyrylium salt, 2,3-dimethyl-6-chloro-benzopyrylium salt, 2,3-dimethyl-6-bromo-benzopyrylium salt, 2-methyl-3-phenyl-benzopyrylium salt, 2-methyl-3-pentyl-benzopyrylium salt, 2-methyl-3-benzyl-benzopyrylium salt, 2,3-dimethyl-8-methoxy-benzopyrylium salt, 2,3-dimethyl-7-methoxy-benzopyrylium salt, 2,3-($\gamma$-tert.-butyl-tetramethylene)-benzopyrylium salt, 2,3-dimethyl-8-carbomethoxy-benzopyrylium salt, 2,3-dimethyl-8-carboethoxy-benzopyrylium salt, 2,3-dimethyl-6-tert.-butyl-benzopyrylium salt, 2,3-dimethyl-6-nitro-benzopyrylium salt, 2,3,6-trimethyl-benzopyrylium salt, 2-methyl-3-nonyl-benzopyrylium salt, 2-methyl-3-phenethyl-benzopyrylium salt, 2-methyl-3-(4'-methylphenyl)-benzopyrylium salt, 2-methyl-3-(4'-chlorophenyl)-benzopyrylium salt, 2,3-($\gamma$-n-octyl-tetramethylene)-benzopyrylium salt, 2,3-($\gamma$-dodecyltetramethylene)-benzopyrylium salt, 2,3-($\gamma$-nonyl-tetramethylene)-benzopyrylium salt, 2,3-($\beta,\gamma,\gamma$-trimethyl-tetramethylene)-benzopyrylium salt, 2,3-trimethylene-benzopyrylium salt, 2,3-pentamethylene-benzopyrylium salt, 2,3-dimethyl-7-methoxy-benzopyrylium salt, 2,3-dimethyl-naphtho[2,1-b]pyrylium salt, 2,3-dimethyl-7-chloro-naphtho[2,1-b]pyrylium salt, 2,3-dimethyl-7-bromo-naphtho[2,1-b]pyrylium salt, 2,3-dimethyl-10-carbomethoxynaphtho[2,1-b]pyrylium salt, 2,3-tetramethylenenaphtho[2,1-b]pyrylium salt, 2,3-(γ-tert.-butyl-tetramethylene)-naphtho[2,1-b]pyrylium salt, 2-methyl-3-i-propyl-naphtho[2,1-b]pyrylium salt, 2-methyl-3-i-butyl-naphtho[2,1-b]pyrylium salt, 2-methyl-3-i-pentyl-naphtho[2,1-b]pyrylium salt and 2,3-dimethyl-10-carboethoxy-naphtho[2,1-b]pyrylium salt.

(b) Aldehydes of the formula III: 4-N,N-dibenzylamino-salicylaldehyde, 4-(N-methyl-N-p-tolyl)-amino-salicylaldehyde, 4-(N-methyl-N-4'-methoxyphenyl)-amino-salicylaldehyde, 4-(N-methyl-N-4'-chlorophenyl)-amino-salicylaldehyde, 4-(N-methyl-N-4'-bromophenyl)-amino-salicylaldehyde, 4-(N-benzyl-N-phenyl)-aminosalicylaldehyde, 4-(N-benzyl-N-4'-chlorophenyl)-amino-salicylaldehyde, 4-(N-ethyl-N-p-tolyl)-amino-salicylaldehyde, 4-(N-methyl-N-4'-ethoxyphenyl)-amino-salicylaldehyde, 4-(N-methyl-N-m-tolyl)-amino-salicylaldehyde, 4-(N-methyl-N-4'-ethylphenyl)-amino-salicylaldehyde, 4-N,N-bis(β-phenylethyl)-amino-salicylaldehyde, 4-(N-benzyl-N-p-tolyl)-amino-salicylaldehyde, 4-(N-n-butyl-N-p-tolyl)-amino-salicylaldehyde, 4-(N-benzyl-N-p-tolyl)-amino-salicylaldehyde, 4-(N-benzyl-N-4'-chlorophenyl)-amino-salicylaldehyde and 4-(N-n-butyl-N-p-tolyl)-amino-salicylaldehyde.

(c) Chalkones of the formula V: 1-o-hydroxyphenyl-2-phenyl-but-1-en-3-one, 1-o-hydroxyphenyl-2-p-tolyl-but-1-en-3-one and 1-o-hydroxyphenyl-2-p-chlorophenyl-but-1-en-3-one.

The manufacture and isolation of the compounds of the formula I is illustrated in the Examples which follow, in which parts and percentages are by weight.

EXAMPLE 1

(a) Production of the pressure-sensitive recording material.

For this purpose, paper is coated with a coating composition comprising 100 parts of the microcapsule dispersion described below, 6 parts of a polymer dispersion, based on acrylic acid esters as the binder, and 6 parts of cellulose powder, using the air-knife process, and the paper is dried. The amount applied is from 5 to 10 g of solids per m² of paper. The other side of the paper can have been coated beforehand with a layer of an electron acceptor (so that it acts as interleaving) or can contain no electron acceptor (and acts as a covering sheet).

Several sheets of the pressure-sensitive copying paper thus obtained are superposed so that the coating containing the microcapsules (underside of the sheet) and the coating containing the electron acceptor touch. When letters are imprinted on the emulsion-coated paper, a clear blue copy is formed on the paper coated with the electron acceptor. At the same time, no color (mirror image) due to the solution of dye-forming component released from the ruptured capsules is formed on the side carrying the microcapsule coating.

If the paper coated on the underside with microcapsules is placed on a paper which has not been coated with an electron acceptor, no color is formed when writing on the paper. If microcapsules which contain the corresponding 7-diethylamino compound instead of the 7-dibenzylamino compound as the dye-forming component are used, a clearly visible bluish violet copy is formed even on paper which has not been coated with an electron acceptor.

(b) Recording material

A solution of 1 part of the dye-forming component prepared as described in (c), in 30 parts of trichlorodiphenyl, is mixed with a solution of 5 parts of gelatin, 2 parts of carboxymethylcellulose and 200 parts of water at from 50° to 60° C. The resulting mixture is converted to an emulsion by rapid stirring and is then brought to a pH of from 8.0 to 8.5. After stirring the emulsion for 20 minutes, the pH is gradually lowered to 3.8 by adding dilute (3% strength) hydrochloric acid. The emulsion is cooled to from 5° to 10° C. whilst continuing the stirring, 5 g of 37% strength formaldehyde solution are added and the batch is stirred for a further hour at from 10° to 20° C. The pH is brought to 9.0 by adding 5% strength sodium hydroxide solution. After stirring for a further hour, a microcapsule dispersion, containing a solution of the above dye-forming component in trichlorodiphenyl, is obtained.

The pH can also be lowered by adding 5% strength acetic acid instead of using hydrochloric acid.

(c) Preparation of the dye-forming component 199 parts of 2,3-dimethyl-benzopyrylium trichlorozincate and 190 parts of 4-dibenzylaminosalicylaldehyde in 1,000 parts of methanol are heated for 3 hours under reflux. The crystalline dye is isolated from the cooled reaction mixture and stirred in 300 parts of 25% strength ammonia solution and 1,000 parts of toluene until it has been completely decolorized. The toluene phase is separated off, dried with sodium sulfate and concentrated to one-fifth. 139 parts of 3'-methyl-7-dibenzyl-amino-2,2'-spirodi-(2H-1-benzopyran) of the formula

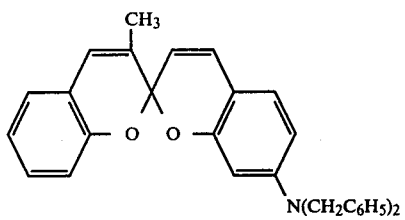

are precipitated from this solution by adding 200 parts of methanol. Melting point 116°–118° C.

EXAMPLE 2

The procedure described in Example 1(a) and (b) is followed, but the dye-forming component described in (c) is used. A pressure-sensitive recording material is obtained, which on inscription whilst in contact with electron acceptors gives a deep blue coloration. On normal paper, which does not contain any electron acceptors, no color is formed on inscription.

(c) Preparation of the dye-forming component 19 parts of 2-methyl-3-i-propyl-benzopyrylium trichlorozincate and 16 parts of 4-dibenzylaminosalicylaldehyde in 100 parts of methanol are heated under reflux for 1½ hours. The crystalline dye is isolated and decolorized as described in Example 1(c). 15 parts of 3'-i-propyl-7-dibenzylamino-2,2'-spirodi(2H-1-benzopyran) of the formula

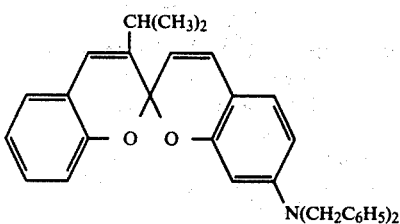

having a melting point of 148°–149° C. are obtained.

EXAMPLE 3

The procedure described in Example 1(a) and (b) is followed, but the dye-forming component described below is used. Blue copies are obtained on paper coated with an electron acceptor.

(c) Preparation of the dye-forming component 16.5 parts of 2,3-dimethyl-benzopyrylium trichlorozincate are condensed with 12 parts of 4-(N-methyl-N-p-tolyl)-amino-salicylaldehyde as described in Example 1(c) and 3 parts of 3'-methyl-7-(N-methyl-N-p-tolyl)-aminospirodi-(2H-1-benzopyran) are obtained.

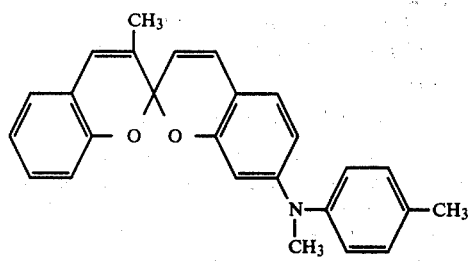

The compound melts at 132°–134° C.

EXAMPLE 4

The procedure described in Example 1(a) and (b) is followed, but the dye-forming component described below is used. Blue copies are obtained on paper coated with an electron acceptor.

(c) Preparation of the dye-forming component 18.6 parts of 2-methyl-3-i-butyl-benzopyrylium trichlorozincate are reacted with 12 parts of 4-(N-methyl-N-p-tolyl)-aminosalicylaldehyde by the method described in Example 1(c); 12.5 parts of 3'-i-butyl-7-(N-methyl-N-p-tolyl)-amino-2,2'-spirodi-(2H-1-benzopyran)

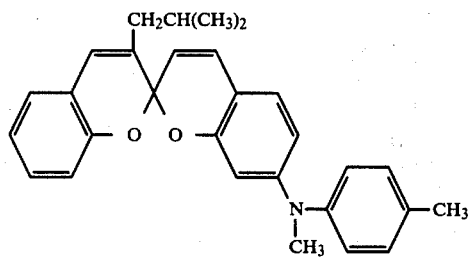

having a melting point of 108°–110° C. are obtained.

EXAMPLE 5

The procedure described in Example 1(a) and (b) is followed, but the dye-forming component described below is used. Blue copies are obtained on paper coated with an electron acceptor.

(c) Preparation of the dye-forming component 21 parts of 2-methyl-3-i-pentyl-benzopyrylium trichlorozincate are condensed with 16 parts of 4-dibenzylamino-salicylaldehyde by the method described in Example 1(c); 19 parts of 3'-i-pentyl-7-dibenzylamino-spirodi-(2H-1-benzopyran)

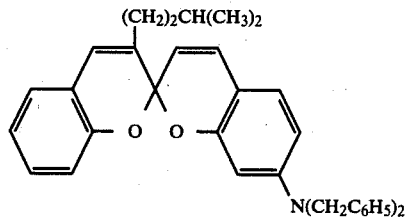

having a melting point of 121°–123° C. are isolated.

EXAMPLE 6

(a) Recording material

A mixture of 2 parts of the dye-forming component obtained as described in (b), 0.1 part of Carnauba wax, 50 parts of dibutyl phthalate and 1 part of polyoxyethylated n-octylphenol is heated at 80°–90° C. until a homogeneous solution is obtained. The melt is applied to paper.

If the paper is placed with the coated side on a paper coated with an acceptor, a clear blue copy is obtained on inscription. When making the copy, virtually no coloration is developed on the coated side.

Equally, no color is formed on a paper which is not coated with an electron acceptor. In contrast, a deep coloration is formed when the 7-diphenylethylamino compound is replaced by the corresponding 7-diethylamino compound.

(b) Preparation of the dye-forming component 17 parts of 2-methyl-3-i-propyl-benzopyrylium trichlorozincate and 19 parts of 4-di-(β-phenylethylamino)-salicylaldehyde are heated in 80 parts of methanol. The resulting crystalline dye is decolorized as described in Example 1(c). 19 parts of 3'-i-propyl-7-diphenethylamino-spirodi-(2H-benzopyran)

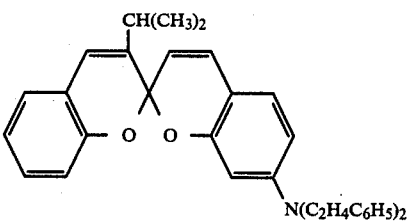

are obtained. The compound melts at 104°–106° C. and gives a blue coloration in contact with acidic materials.

EXAMPLE 7

(a) Recording material (a1) The procedure described in Example 1(a) and (b) is followed, but the dye-forming component described below is used.

(a2) The procedure described in Example 6(a) is followed and a copying paper coated with dye-forming component is obtained.

The material obtained as described in (a1) and (a2) gives blue copies on inscription in contact with an electron acceptor.

(c) Preparation of the dye-forming component 21 parts of 2-methyl-3-benzyl-benzopyrylium trichlorozincate and 16 parts of 4-dibenzylaminosalicylaldehyde in 160 parts of methanol are refluxed for 2 hours. The crystalline dye obtained is decolorized as described in Example 1. 10 parts of 3'-benzyl-7-dibenzylaminospirodi-(2H-1-benzopyran)

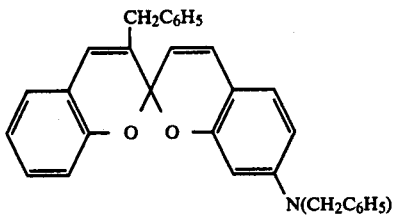

having a melting point of 185°–186° C. are obtained.

In contact with acidic materials, a blue coloration is obtained.

EXAMPLE 8

The procedure described in Example 1(a) and (b) is followed, but the dye-forming component described below is used. Blue copies are obtained on paper coated with an electron acceptor.

(c) Preparation of the dye-forming component 39 parts of 2-methyl-3-phenyl-benzopyrylium trichlorozincate are reacted with 32 parts of 4-dibenzylaminosalicylaldehyde by the method described in Example 1(c); 14 parts of 3'-phenyl-7-dibenzylaminospirodi-(2H-1-benzopyran)

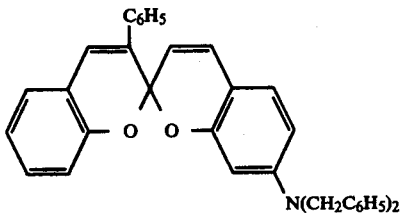

having a melting point of 154°–156° C. are isolated.

In contact with acidic materials, the compound develops a blue coloration.

EXAMPLE 9

The procedure described in Example 1(a) and (b) is followed, but the dye-forming component described below is used. Blue copies are obtained on paper coated with an electron acceptor.

(c) Preparation of the dye-forming component 26 parts of 2,3-dimethyl-benzopyrylium trichlorozincate are condensed with 33 parts of 4-(N-methyl-N-p-chlorophenyl)-aminosalicylaldehyde by the method described in Example 1(c). 7 parts of 3-methyl-7-(N-methyl-N-p-chlorophenyl)-amino-spirodi-(2H-1-benzopyran)

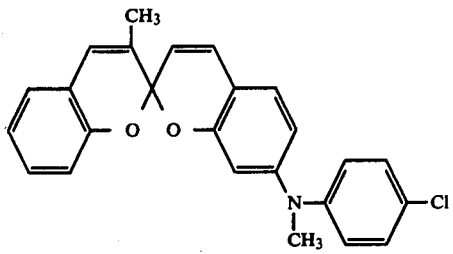

having a melting point of 166°–168° C. are obtained. In contact with acidic materials, the compound develops a blue coloration.

EXAMPLES 10 to 41

The procedure of Example 1(a) and (b), 6(a) or 46(a) and (b) is followed, using as the dye-forming component a compound of the formula

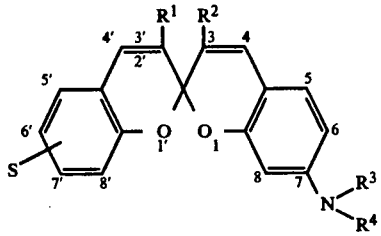

The meanings of the substituents S, $R^1$, $R^2$, $R^3$ and $R^4$ and the hues developed on contact with acidic materials are shown in the Table which follows.

| No. | S | $R^1$ | $R^2$ | $R^3$ | $R^4$ | Hue |
|-----|---|-------|-------|-------|-------|-----|
| 10 | — | —$CH_3$ | —H | —$CH_2C_6H_5$ | p-$ClC_6H_4$— | blue |
| 11 | — | —$C_{10}H_{21}(n)$ | —H | " | $CH_2C_6H_5$— | " |
| 12 | 6'-Cl | —$CH_3$ | —H | " | " | " |
| 13 | 6'-Br | " | —H | " | " | " |
| 14 | — | —($CH_2$)$_3$— | | " | " | " |
| 15 | — | —$CH_2$—$\overset{\overset{C_4H_9(tert.)}{\mid}}{CH}$—$CH_2$— | | " | " | " |
| 16 | — | —$CH_2$—$\overset{\overset{C_8H_{17}(n)}{\mid}}{CH}$—$CH_2$— | | " | " | violet |
| 17 | — | —$CH_2$—$\overset{\overset{C_9H_{19}(n)}{\mid}}{CH}$—$CH_2$— | | " | —$CH_2C_6H_5$ | " |
| 18 | — | —$CH_2$—$\overset{\overset{C_{12}H_{25}(n)}{\mid}}{CH}$—$CH_2$— | | " | " | " |
| 19 | 8'-$CO_2CH_3$ | —$CH_3$ | —H | " | " | blue |
| 20 | 6'-$C_4H_9$(tert.) | " | —H | " | " | " |
| 21 | 6'-$NO_2$ | " | —H | " | " | bluish violet |
| 22 | 8'-$CO_2C_2H_5$ | " | —H | " | " | blue |
| 23 | — | p-$H_3CC_6H_4$— | —H | " | " | " |

-continued

| No. | S | R¹ | R² | R³ | R⁴ | Hue |
|---|---|---|---|---|---|---|
| 24 | — | p-ClC₆H₄— | —H | " | " | " |
| 25 | — | —C₂H₄C₆H₅ | —H | " | " | " |
| 26 | — | —CH₃ | —H | —CH₃ | p-BrC₆H₅— | " |
| 27 | — | —CH—CH₂—C(CH₃)₂—  (with CH₃ branches) | CH₃ | —CH₂C₆H₅ | —CH₂C₆H₅ | reddish violet |
| 28 | 6'-CH₃ | —CH₃ | —H | " | " | blue |
| 29 | — | —(CH₂)₂— | | " | " | violet |
| 30 | — | —(CH₂)₄— | | " | " | " |
| 31 | — | —CH₃ | —H | —C₂H₅ | p-H₃CC₆H₄— | blue |
| 32 | — | —CH(CH₃)₂ | —H | —CH₃ | p-H₅C₂OC₆H₄— | " |
| 33 | — | —CH₃ | —H | " | p-H₃COC₆H₄— | " |
| 34 | — | " | —H | " | p-H₅C₂C₆H₄— | " |
| 35 | — | —CH(CH₃)₂ | —H | " | m-H₃CC₆H₄— | |
| 36 | — | —CH₃ | —H | —CH₂C₆H₅ | p-H₃CC₆H₄— | |
| 37 | — | " | —H | " | —C₆H₅ | " |
| 38 | — | —CH₃ | —H | —C₄H₉(n) | p-H₃CC₆H₄— | blue |
| 39 | — | —C₅H₁₁(n) | —H | —CH₂C₆H₅ | —CH₂C₆H₅ | " |
| 40 | 7'-OCH₃ | —CH₃ | —H | " | " | bluish green |
| 41 | 8'-OCH₃ | " | —H | " | " | blue |

EXAMPLE 42

The procedure described in Example 1(a) and (b) is followed, but the dye-forming component described below is used. On paper coated with an electron acceptor, bluish green copies are obtained.

(c) Preparation of the dye-forming component 21 parts of 2-methyl-3-i-butyl-naphthopyrylium trichlorozincate and 16 parts of 4-dibenzylamino-salicylaldehyde in 130 parts of methanol are refluxed for 45 minutes. The crystalline dye is isolated and stirred in 100 parts of 25% strength ammonia solution and 300 parts of toluene until completely decolorized. The toluene phase is separated off, dried over sodium sulfate and concentrated to one-fifth. In order to precipitate the dye-forming component completely, 100 parts of methanol are added, and 19 parts of 3'-i-butyl-7-dibenzylaminospiro-(2H-1-benzopyran)-2,2'-(2H)naphtho-(2,1-b)-pyran

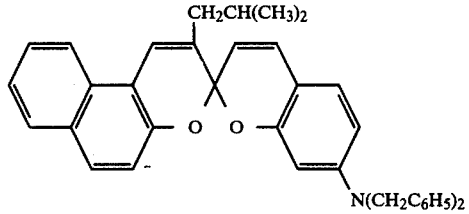

having a melting point of 184°–186° C. are obtained.

In contact with acidic materials, a bluish green coloration is obtained.

EXAMPLE 43

The procedure described in Example 1(a) and (b) is followed, but the dye-forming component described below is used. On paper coated with an electron acceptor, bluish green copies are obtained.

(c) Preparation of the dye-forming component

Using the procedure of Example 42, 23 parts of 2-methyl-3-i-pentyl-naphthopyrylium trichlorozincate are reacted with 16 parts of 4-dibenzyl-aminosalicylaldehyde. 4 parts of 3'-i-pentyl-7-dibenzylamino-spiro-(2H-1-benzopyran)-2,2'-(2H)-naphtho-(2,1-b)-pyran

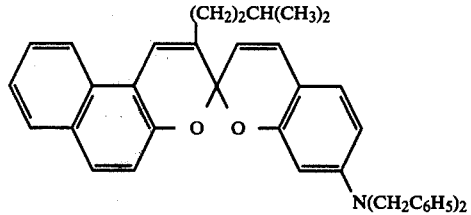

are obtained. The dye-forming component melts at 175° C. and develops a bluish green coloration with electron acceptors.

EXAMPLE 44

The procedure described in Example 1(a) and (b) is followed, but the dye-forming component described below is used. On paper coated with an electron acceptor, bluish green copies are obtained.

(c) Preparation of the dye-forming component 19 parts of 2,3-dimethyl-naphthopyrylium trichlorozincate are condensed with 16 parts of 4-dibenzylaminosalicylaldehyde using the method described in Example 42(c); 20 parts of 3'-methyl-7-dibenzylamino-spiro-(2H-1-benzopyran)-2,2'-(2H)-naphtho-(2,1-b)-pyran

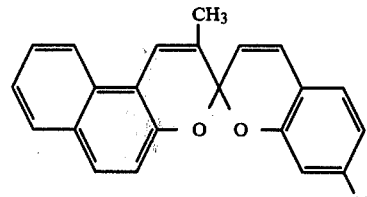

having a melting point of 108°–110° C. are obtained.

In contact with acidic materials, a bluish green coloration is obtained.

EXAMPLE 45

The procedure described in Example 1(a) and (b) is followed, but the dye-forming component described below is used. On paper coated with an electron acceptor, bluish green copies are obtained.

(c) Preparation of the dye-forming component

Following the procedure described in Example 42c, 19 parts of 2,3-dimethyl-naphthopyrylium trichlorozincate are condensed with 17 parts of 4-di-(β-phenylethylamino)-salicylaldehyde. 18 parts of 3′-methyl-7-diphenethylamino-spiro-(2H-1-benzopyran)-2,2′-(2H)-naphtho-(2,1b)-pyran

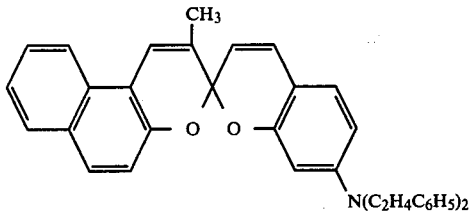

having a melting point of 163°–165° C. are obtained.

In contact with acidic materials, the compound develops a blue coloration.

EXAMPLE 46

(a) Recording material

The microcapsule dispersion described under (b) is applied to paper in the form of a coating composition comprising 100 parts of the microcapsule dispersion obtained as described in (b), 6 parts of a polymer dispersion based on acrylic acid esters and 6 parts of cellulose flour. 7–10 g of solids/m² are applied.

Sharp blue copies are obtained on paper coated with an electron acceptor. The dye-forming component released from the capsules gives virtually no color reaction with the coating which contains the capsules.

If the paper coated with microcapsules on the underside is placed on a paper not coated with an electron acceptor, no copy is obtained on inscription. If, in contrast, microcapsules which contain the corresponding 7-diethylamino compound instead of the 7-N-methyl-N-p-tolyl-amino compound are used, a distinctly visible blue copy is obtained.

(b) Preparation of the microcapsule dispersion

Following the procedure described in German Pat. No. 2,119,933, Example 5, a solution of 3 parts of the dye-forming component from Example 46(c), 0.5 part of tributylamine, 180 parts of chloroform, 90 parts of trichlorodiphenyl, 10 parts of gasoline (boiling range 155°–185° C.) and 60 parts of a 40% strength solution of the wall material (prepared as described in Example 1 of the said German Patent) is dispersed by means of an Ultra-Turrax (a registered trademark) in a solution of 345 parts of water and 5 parts of polyvinylpyrrolidone. The dispersion obtained is mixed with a solution of 5 parts of polyvinylpyrrolidone (K value 90) in 295 parts of water and 0.2 part of p-toluenesulfonic acid; the solvents are removed by distillation and the microcapsules obtained are hardened by adding formaldehyde.

The resulting microcapsule dispersion is coated on to paper and dried. This paper gives sharp blue copies on paper coated with an electron acceptor. The dye-forming component released from the capsules gives virtually no color reaction with the coating which contains the capsules.

(c) Preparation of the dye-forming component 19 parts of 2,3-dimethyl-naphtho-pyrylium trichloroazincate are condensed with 12 parts of 4-(N-methyl-N-p-tolyl)-amino-salicylaldehyde as described in Example 42(c). After isolation, 15 parts of 3′-methyl-7-(N-methyl-N-phenyl)-amino-spiro-(2H)-1-benzopyran)-2,2′-(2H)-naphtho-(2,1-b)-pyran

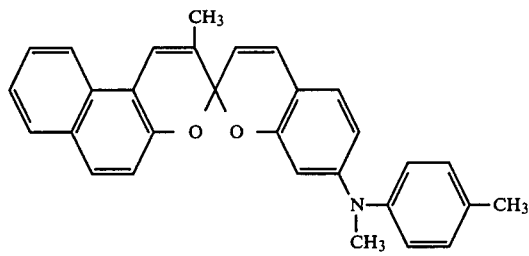

having a melting point of 175°–177° C. are obtained.

EXAMPLES 47 to 53

The procedure described in Example 46(a) and (b), Example 1(a) and (b) or Example 6(a) is followed, but with a dye-forming component of the formula

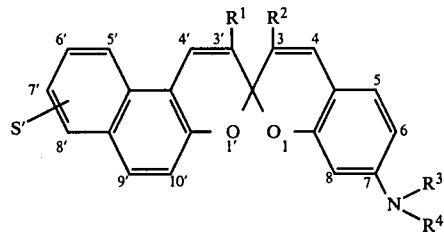

The meanings of the substituents S′, $R^1$, $R^2$, $R^3$ and $R^4$ and the hues developed on contact with acidic materials are shown in the Table which follows.

| No. | S′ | $R^1$ | $R^2$ | $R^3$ | $R^4$ | Hue |
|---|---|---|---|---|---|---|
| 47 | — | —(CH$_2$)$_3$— | | —CH$_2$C$_6$H$_5$ | —CH$_2$C$_6$H$_5$ | blue |
| 48 | 7′-Cl | —CH$_3$ | —H | —CH$_3$ | p-H$_3$CC$_6$H$_4$— | ″ |
| 49 | 7′-Br | ″ | —H | —CH$_2$C$_6$H$_5$ | —CH$_2$C$_6$H$_5$ | bluish green |
| 50 | 10′—COCH$_3$ | ″ | —H | ″ | ″ | blue |
| 51 | — | —CH(CH$_3$)$_2$ | —H | —CH$_3$ | p-Cl—C$_6$H$_4$— | ″ |
| 52 | — | ″ | —H | —CH$_2$C$_6$H$_5$ | —CH$_2$C$_6$H$_5$ | bluish green |
| 53 | — | ″ | —H | —CH$_3$ | p-H$_3$CC$_6$H$_4$— | blue |

EXAMPLE 54

The procedure described in Example 46(a) and (b) is followed, but the dye-forming component described below is used. Blue sharp copies are obtained on paper coated with an electron acceptor. The same dye-forming component can be used equally successfully for preparing recording materials by the methods described in Example 1(a) and (b) or in Example 6(a). Here again, blue copies are obtained.

(c) Preparation of the dye-forming component 25 parts of 2-methyl-3-cetyl-benzopyrylium trichlorozincate are reacted with 16 parts of 4-dibenzylaminosalicylaldehyde by the method described in Example 1(c); 6 parts of 3'-cetyl-7-dibenzylamino-2,2'-spirodi-(2H-1-benzopyran) of the formula

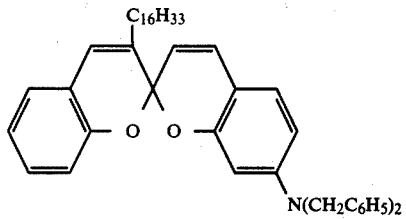

having a melting point of 102°–104° C. are obtained.

With electron acceptors, the compound gives a blue coloration.

We claim:

1. A pressure-sensitive recording material comprising a substrate coated with a dye-forming component and a binder which permits release of the dye-forming component upon the application of pressure to the substrate, wherein the dye-forming component is a spirodipyran of the formula

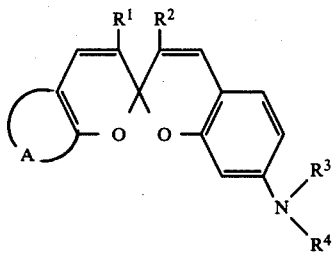

where A is the radical of a fused benzene ring which is unsubstituted or substituted by alkyl of 1 to 4 carbon atoms, alkoxy of 1 to 4 carbon atoms, nitro, chlorine, bromine or carbo-alkoxy (where alkoxy is of 1 to 6 carbon atoms) or is the radical of a naphthalene ring which is fused in the 2,1-position and is unsubstituted or substituted by chlorine, bromine or carboalkoxy (where alkoxy is of 1 to 6 carbon atoms), $R^1$ is alkyl of 1 to 16 carbon atoms, phenyl, which is unsubstituted or substituted by alkyl of 1 to 4 carbon atoms, alkoxy of 1 to 4 carbon atoms, chlorine or bromine, or phenylalkyl of 7 to 10 carbon atoms, $R^2$ is hydrogen or $R^1$ and $R^2$ together are a trimethylene or tetramethylene bridge, which is unsubstituted or in which one, two or three H atoms are substituted by alkyl of 1 to 12 carbon atoms, $R^3$ is benzyl or β-phenylethyl and $R^4$ is benzyl, β-phenylethyl or phenyl which is unsubstituted or substituted by chlorine, bromine, alkyl of 1 to 4 carbon atoms, methoxy or ethoxy, $R^3$ and $R^4$ being identical or different, or $R^3$ is alkyl of 1 to 4 carbon atoms and $R^4$ is phenyl which is unsubstituted or substituted by chlorine, bromine, alkyl of 1 to 4 carbon atoms, methoxy or ethoxy, or $R^3$ is benzyl and $R^4$ is β-cyanoethyl.

2. A pressure-sensitive recording material as claimed in claim 1, wherein the substrate is a paper web which consists of cellulose fibers, of a mixture of cellulose fibers and synthetic fibers, or of synthetic fibers only.

3. A pressure-sensitive recording material as claimed in claim 1, wherein the dye-forming component is in the form of a solution or suspension enclosed in microcapsules.

4. A pressure-sensitive recording material as claimed in claim 1, wherein, in the dye-forming component, $R^3$ and $R^4$ are benzyl or β-phenylethyl, or $R^3$ is alkyl of 1 to 4 carbon atoms and $R^4$ is 4-chlorophenyl or 4-alkylphenyl, where alkyl is of 1 to 4 carbon atoms.

5. A pressure-sensitive recording material comprising a paper web as substrate, coated with a dye-forming component and a binder which permits release of the dye-forming component upon the application of pressure to the substrate, wherein the dye-forming component is a spirodipyran of the formula

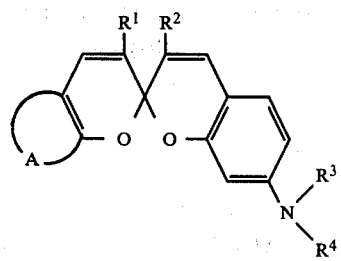

where $R^1$ is alkyl of 1 to 4 carbon atoms, $R^2$ is hydrogen, $R^3$ and $R^4$ are benzyl or β-phenylethyl or $R^3$ is alkyl of 1 to 4 carbon atoms and $R^4$ is 4-chlorophenyl or 4-alkylphenyl, where alkyl is of 1 to 4 carbon atoms, and A is the radical of a fused benzene ring which is unsubstituted or is substituted by alkyl of 1 to 4 carbon atoms, alkoxy of 1 to 4 carbon atoms, nitro, chlorine, bromine or carbo-alkoxy (where alkoxy is of 1 to 6 carbon atoms) or is a naphthalene ring, fused in the 2,1-position, which is unsubstituted or substituted by chlorine, bromine or carboalkoxy (where alkoxy is of 1 to 6 carbon atoms).

6. A pressure-sensitive recording material as claimed in claim 5, wherein, in the dye-forming component, $R^3$ and $R^4$ are benzyl or $R^3$ is methyl and $R^4$ is 4-chlorophenyl or 4-alkylphenyl (where alkyl is of 1 to 4 carbon atoms).

7. A pressure-sensitive recording material as claimed in claim 5, wherein, in the dye-forming component, $R^3$ and $R^4$ are benzyl or $R^3$ is methyl and $R^4$ is 4-methylphenyl and A is the radical or a fused benzene ring or fused naphthalene ring.

8. A pressure sensitive copying system comprising a substrate coated with a dye-forming component and a binder which permits release of the dye-forming component upon the application of pressure to the substrate, wherein the dye-forming component is a spirodipyran of the formula

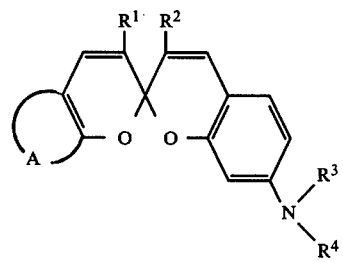

where A is the radical of a fused benzene ring which is unsubstituted or substituted by alkyl of 1 to 4 carbon atoms, alkoxy of 1 to 4 carbon atoms, nitro, chlorine, bromine or carbo-alkoxy (where alkoxy is of 1 to 6 carbon atoms) or is the radical of a naphthalene ring which is fused in the 2,1-position and is unsubstituted or substituted by chlorine, bromine or carboalkoxy (where alkoxy is of 1 to 6 carbon atoms), $R^1$ is alkyl of 1 to 16 carbon atoms, phenyl, which is unsubstituted or substituted by alkyl of 1 to 4 carbon atoms, alkoxy of 1 to 4 carbon atoms, chlorine or bromine, or phenylalkyl of 7 to 10 carbon atoms, $R^2$ is hydrogen or $R^1$ and $R^2$ together are a trimethylene or tetramethylene bridge, which is unsubstituted or in which one, two or three H atoms are substituted by alkyl of 1 to 12 carbon atoms, $R^3$ is benzyl of β-phenylethyl and $R^4$ is benzyl, β-phenylethyl or phenyl which is unsubstituted or substituted by chlorine, bromine, alkyl of 1 to 4 carbon atoms, methoxy or ethoxy, $R^3$ and $R^4$ being identical or different, or $R^3$ is alkyl of 1 to 4 carbon atoms and $R^4$ is phenyl which is unsubstituted or substituted by chlorine, bromine, alkyl of 1 to 4 carbon atoms, methoxy or ethoxy, or $R^3$ is benzyl and $R^4$ is β-cyanoethyl and a substrate coated with an electron acceptor.

9. A pressure sensitive copying system comprising a paper web as substrate, coated with a dye-forming component and a binder which permits release of the dye-forming component upon the application of pressure to the substrate, wherein the dye-forming component is a spirodipyran of the formula

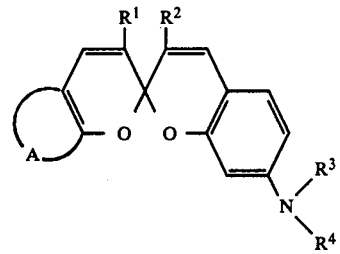

where $R^1$ is alkyl of 1 to 4 carbon atoms, $R^2$ is hydrogen, $R^3$ and $R^4$ are benzyl or β-phenylethyl or $R^3$ is alkyl of 1 to 4 carbon atoms and $R^4$ is 4-chlorophenyl or 4-alkylphenyl, where alkyl is of 1 to 4 carbon atoms, and A is the radical of a fused benzene ring which is unsubstituted or is substituted by alkyl of 1 to 4 carbon atoms, alkoxy of 1 to 4 carbon atoms, nitro, chlorine, bromine or carbo-alkoxy (where alkoxy is of 1 to 6 carbon atoms) or is a naphthalene ring, fused in the 2,1-position, which is unsubstituted or substituted by chlorine, bromine or carboalkoxy (where alkoxy is of 1 to 6 carbon atoms) and a substrate coated with an electron acceptor.

10. The pressure sensitive copying system of claim 9, wherein, in the dye-forming component, $R^3$ and $R^4$ are benzyl or $R^3$ is methyl and $R^4$ is 4-chlorophenyl or 4-alkylphenyl (where alkyl is of 1 to 4 carbon atoms).

11. The pressure sensitive copying system of claim 9, wherein, in the dye-forming component, $R^3$ and $R^4$ are benzyl or $R^3$ is methyl and $R^4$ is 4-methylphenyl and A is the radical of a fused benzene ring or fused naphthalene ring.

* * * * *